(12) United States Patent
Goumont et al.

(10) Patent No.: US 6,228,237 B1
(45) Date of Patent: May 8, 2001

(54) AUTOMATIC MEASURING DEVICE FOR THE CONCENTRATION OF A DEVELOPING AGENT

(75) Inventors: Claude G. Goumont, Mellecey; Jacques Roussilhe, Virey le Grand; Gerard R. Sirand-Rey, Chalon sur Saone, all of (FR)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/264,184

(22) Filed: Mar. 8, 1999

(30) Foreign Application Priority Data

Mar. 13, 1998 (FR) .................................................. 98 03329

(51) Int. Cl.$^7$ ................................................. G01N 27/403
(52) U.S. Cl. .......................... 204/412; 204/406; 204/435; 324/714; 396/578
(58) Field of Search .................................. 204/406, 412, 204/407, 435, 415; 205/775, 787; 324/714; 396/578

(56) References Cited

U.S. PATENT DOCUMENTS

| 3,957,592 | 5/1976 | Young . |
| 3,959,108 | 5/1976 | Plumpe, Jr. . |
| 4,279,728 | * 7/1981 | Horii ..................................... 204/416 |
| 4,686,011 | * 8/1987 | Jaeckle ................................. 204/401 |
| 5,346,605 | * 9/1994 | Wolcott et al. ....................... 204/412 |
| 5,597,473 | * 1/1997 | Hambitzer et al. ............... 205/780.5 |

FOREIGN PATENT DOCUMENTS

| 288 255 | 3/1991 | (DE) . |
| 2 273 277 | 12/1975 | (FR) . |

OTHER PUBLICATIONS

K. Brunt; "New Electrochemical Detector for High–performance Liquid Chromatography", Journal of Chromatography, vol. 161, 1978, pp. 310–314.

* cited by examiner

Primary Examiner—Robert J. Warden, Sr.
Assistant Examiner—Kaj K. Olsen
(74) Attorney, Agent, or Firm—David A. Novais

(57) ABSTRACT

A device for automatically measuring a concentration of a developing agent in a developing bath includes a voltage generator capable of generating at least one voltage ramp provided to feed a three-electrode cell; a potentiostat provided to maintain a constant potential difference between two electrodes; a peak detector provided to identify the maximum current flowing in the three-electrode cell that corresponds to the developing agent concentration; and a display unit provided to show the maximum current.

5 Claims, 4 Drawing Sheets

AUTOMATIC MEASURING DEVICE FOR THE CONCENTRATION OF A DEVELOPING AGENT

FIELD OF THE INVENTION

This invention relates to the automatic measurement of the concentration of a developing agent in a developing bath, and in particular to a device for automatically measuring the concentration of a developing agent.

BACKGROUND OF THE INVENTION

Developing baths for photographic films comprise developing agents that are reducing compounds. As it is used, the developing bath becomes depleted in developing agent due to the development itself(redox reaction), and also due to aerial oxidation. This decrease of developing agent concentration causes a reduction of bath activity. In order to maintain bath activity, the bath has to be regularly replenished so as not to alter the quality of the developed products. However, it is desirable to replenish it so as to compensate solely for the variation of developing agent concentration. For this reason, regular and fast measurement of developing agent concentration in developing baths is desired.

Procedures for measuring the concentration of developing agents are known that include using a voltammetric method. Three-electrode cells are used to take measurements; they comprise three electrodes not fixed one to another. The operator who carries out the measurement arranges the electrodes in relation to one another in a position that allows correct measurement. One problem that occurs with this use is that the variation of position of the electrodes in relation one to another causes variations of the measurements. Another problem that occurs with this type of cell is that the measurement cannot be taken directly in the solution containing the developing agents. The solution is sampled and added into the cell. But the reaction continues to take place in the time that the solution is sampled and added into the cell. Thus the measurement that is taken in the cell does not allow the developing agent concentration in the developing bath to be obtained accurately. Furthermore, aerial oxidation can take place during the sampling.

On the other hand, procedures for measuring developing agent concentration that include using a voltammetric method use expensive apparatuses, which also requires operators to know about the chemical reactions that are taking place in developing baths and a certain number of adjustments.

SUMMARY OF THE INVENTION

An object of the present invention is to develop a device for measuring the concentration of a developing agent that does not have the drawbacks described above, and in particular a mobile device that is easy to use and has a low cost.

The invention relates to a device for automatically measuring a concentration of a developing agent in a developing bath. The device comprises a voltage generator capable of generating at least one voltage ramp for feeding a three-electrode cell; a potentiostat provided to maintain constant potential difference between two electrodes; a peak detector provided to identify the maximum current flowing in the three-electrode cell that corresponds to the concentration of the developing agent; and a display unit provided to show the maximum current.

BRIEF DESCRIPTION OF THE DRAWINGS

Other characteristics will appear on reading the description below, making reference to the drawings wherein.

DETAILED DESCRIPTION OF THE INVENTION

The device according to the present invention uses the voltammetric principle to measure the concentration of a developing agent. A three-electrode cell is provided to be put into contact with the developing bath containing the developing agent whose concentration is to be measured. Current variations relative to the voltage applied to the terminals of the three-electrode cell are measured. The curve obtained has a peak or a plateau whose height is proportional to the developing agent concentration.

Figure 1:
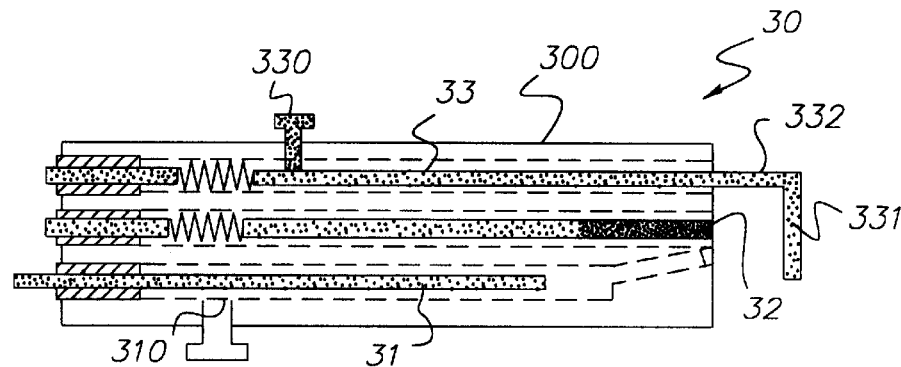
FIG. 1 shows a cross-section of the electrode cell of the present invention.

A three-electrode cell 30 used in the device of the present invention and shown in FIG. 1 comprises one reference electrode 31, one indicator electrode 32, and one auxiliary electrode 33. The voltage between the indicator electrode 32 and the auxiliary electrode 33 is controlled so as to maintain the potential difference constant between the indicator electrode 32 and the reference electrode 31, as will be described below.

The three-electrode cell 30 is a compact cell that comprises a holder 300 fitted with three housing units, each housing unit being designed to accommodate one specific electrode. The holder 300 keeps the three electrodes 31, 32, 33 in fixed positions in relation to one another, the three electrodes appearing at one end of the holder 300. The reference electrode 31 is arranged so that its end is as close as possible to the end of the indicator electrode 32 so that the potential at the end of these two electrodes is approximately the same. The distance between the ends of the reference 31 and indicator 32 electrodes is for example in the order of one millimeter. The auxiliary electrode 33 is arranged so that the lines of current that flow between the indicator electrode 32 and the auxiliary electrode 33 are parallel and uniform. The auxiliary electrode 33 has for example an angled end 331, parallel to the surface of the end of the holder from which the three electrodes appear. The non-angled part 332 of the auxiliary electrode 33 is located outside the holder 300. A non-angled part 332 of the auxiliary electrode 33 located outside the holder 300 is electrically insulated in order to prevent disturbance in the current lines.

The reference electrode 31 comprises a chlorinated silver rod immersed in a potassium chloride solution saturated in silver chloride. The housing unit provided to accommodate the reference electrode 31 has a straight part wherein the silver rod is located, and an oblique part comprising the end which approaches the end of the indicator electrode 32. The potassium chloride is added to the cavity through an orifice 310. The indicator electrode 32 can be made of platinum, gold or vitreous carbon. Preferably vitreous carbon will be selected. The auxiliary electrode 33 can be of any material so long as its electrochemical properties do not affect the performance of the relevant electrode. For example it can be stainless steel. A screw 330 is provided to attach the auxiliary electrode 33 to the holder 300. The auxiliary electrode 33 can be removed from the holder 300 by loosening the screw 330, particularly when the indicator electrode 32 has to be polished.

The holder 300 that holds the three electrodes is made of an electrically insulating and photographically inert material. For example Teflon® can be selected.

When the invention measuring device is used the three-electrode cell (30) is immersed directly into the developing bath. The measurement is almost immediate (it takes about 10 seconds) and shows the actual concentration of the developing agent at the moment of measuring. Also, the cell is easy to use because it does not require any adjustment.

Figure 2:
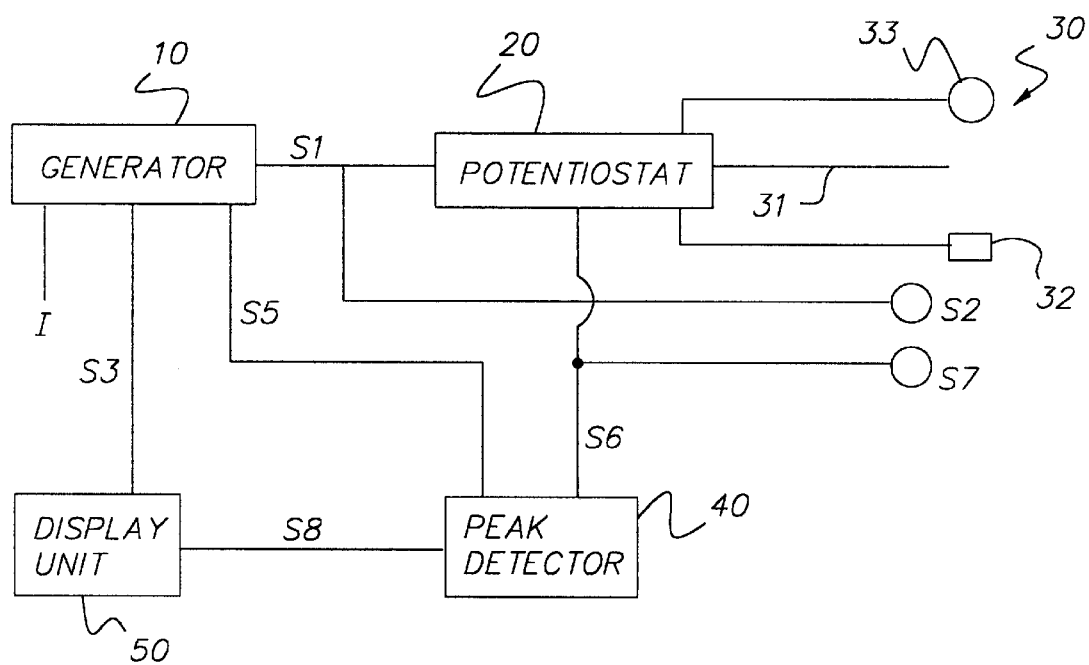
FIG. 2 shows a block diagram of the device of the present invention.

Reference is now made to FIG. 2 which is a block diagram of the device of the present invention. First, the device comprises a generator 10 capable of generating a voltage ramp. The three-electrode cell described above is fitted with a potentiostat 20 provided to maintain a constant potential difference between the indicator electrode 32 and the reference electrode 31. As the developing agent concentration is proportional to the height of the plateau of the current-voltage curve, the current that flows between the indicator electrode 32 and the auxiliary electrode 33 is transmitted to a peak detector 40, which only records the maximum value. A display unit 50 finally enables the value of the maximum current measured to be seen.

Figure 3:
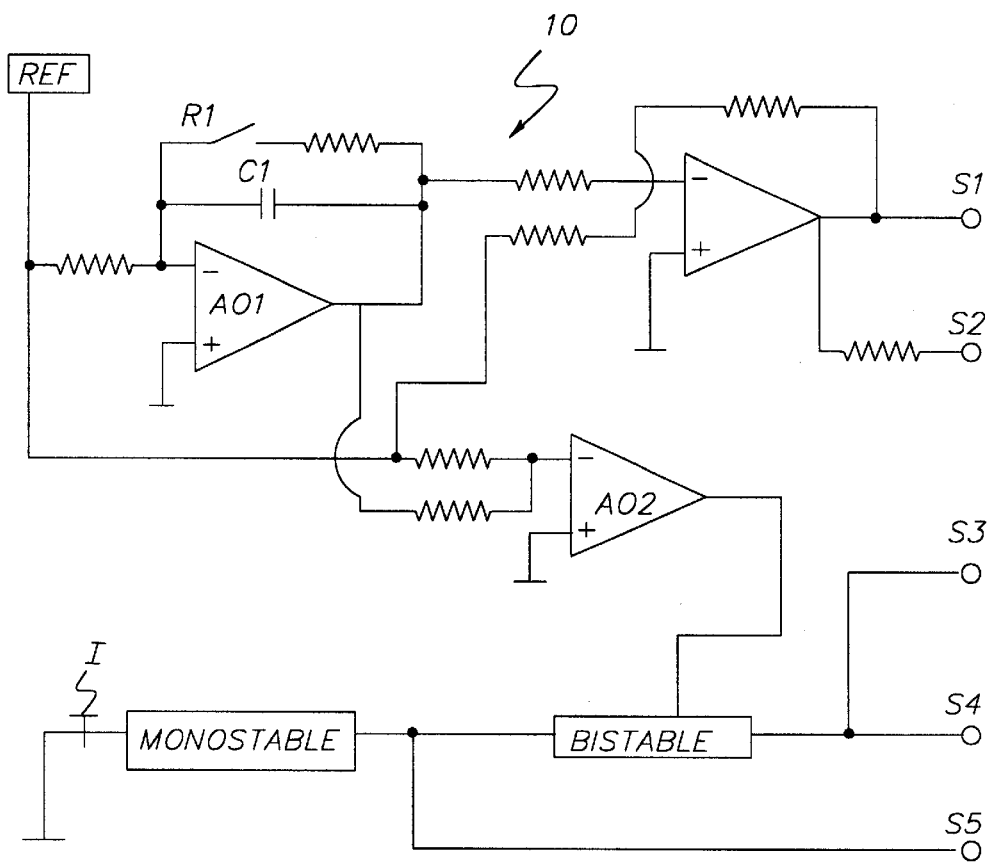
FIG. 3 shows a block diagram of the voltage generator.

In one embodiment, the device of the present invention comprises the voltage ramp generator 10 as shown in FIG. 3. So as to cover all the potentiometric phenomena corresponding to the developing agent to be monitored, a voltage ramp is defined that allows the peak or plateau characteristic of the developing agent concentration to be observed. The voltage sweep speed must be constant. If the sweep speed setting is too low, the measurement will take too long and moreover, the phenomenon measured will be low because it is proportional to the sweep speed. If the sweep speed setting is too high, there is a risk of not observing the phenomena to be measured. The sweep speed is between 10 and 500 mV/s, and can be for example in the order of 100 mV/s.

The ramp generator 10 is supplied at ±6V. A stable internal voltage reference, REF, enables the voltage at the start and end of the ramp as well as the ramp speed to be set. The voltage ramp obtained at output s1 of the generator 10 is between +0.5V and −0.5V, the input to the potentiostat 20 being at the same potential as s1. An auxiliary output s2 representing the ramp voltage is provided for connection for example to a plotter.

One push-button I is provided to trigger a pulse. When there is a pulse, a monostable device closes (s5) a relay R2, shown in FIG. 5, and holds it closed for a set time t. A capacitor C2 mounted in parallel with R2 is thus discharged during the time t. The apparatus is then reset to zero and a measurement can start. After the time t, the relay R2 is open and is not longer supplied, which allows the capacitor C2 to charge. A bistable device, shown in FIG. 3, enables control (s4) of a relay R1 by opening it in order to start the ramp. A capacitor C1, mounted in parallel with R1, charges, which causes the output voltage of an amplifier AO1 to increase. A comparator amplifier AO2 connected to the output of AO1 allows detection of when the ramp has reached a set value corresponding to the ramp end. When the set voltage is reached, the bistable device returns to its preceding state where it controls the closing of the relay R1. The voltage ramp is stopped and the voltage goes to zero. Also, an output s3 is connected to the display unit 50. While the ramp is active, s3 has a first state that allows the display unit 50 to show a succession of varying values. When the ramp has ended, the output s3 has a second state that allows the display unit to show only the last value read.

Figure 4:
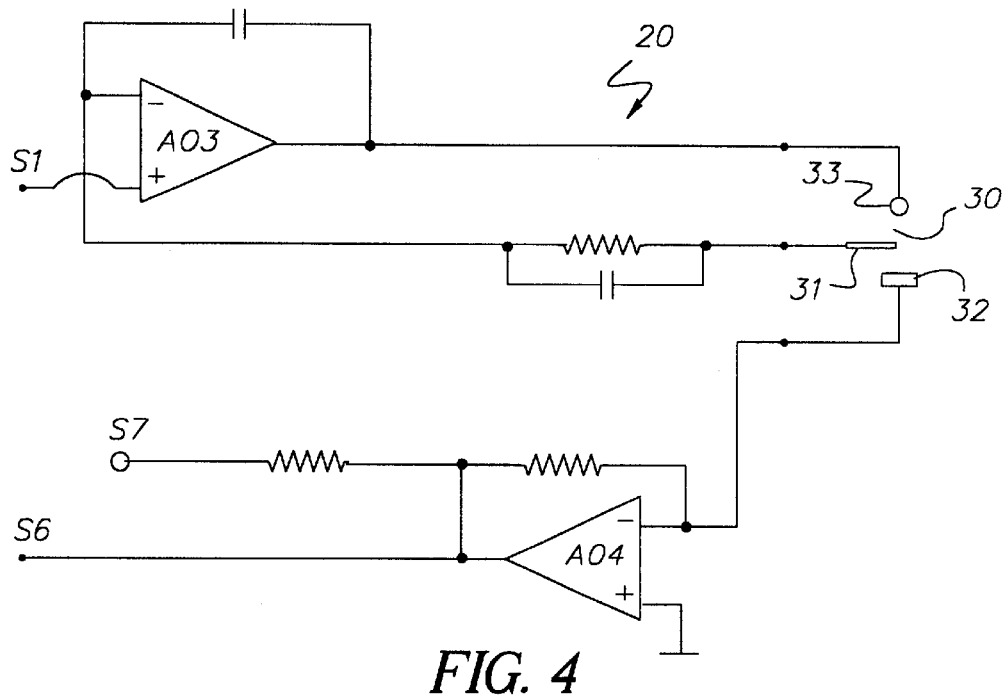
FIG. 4 shows a block diagram of the potentiostat.

FIG. 4 shows a block diagram of the potentiostat 20. The potentiostat 20 is provided to maintain a constant potential difference between the indicator electrode 32 and the reference electrode 31. The output s1 of the ramp generator 10 allows one input to an operational amplifier AO3 of the potentiostat 20 to be at the ramp potential. The operational amplifier AO3 controls the voltage of the auxiliary electrode 33 so as to obtain a potential on the reference electrode 31 the same as that supplied by the ramp generator 10. The response of the electrochemical system is in current form. This current is converted into voltage through a second operational amplifier AO4 used as a current-voltage converter. The amplifier AO4 then delivers a voltage proportional to the current crossing the three-electrode cell 30. The output s6 of the potentiostat 20 is connected to one input to the peak detector 40, so as to apply to it the voltage proportional to the current crossing the three-electrode cell. One auxiliary output s7 representing the current that crosses the three-electrode cell is provided for connection for example to a plotter.

Figure 5:
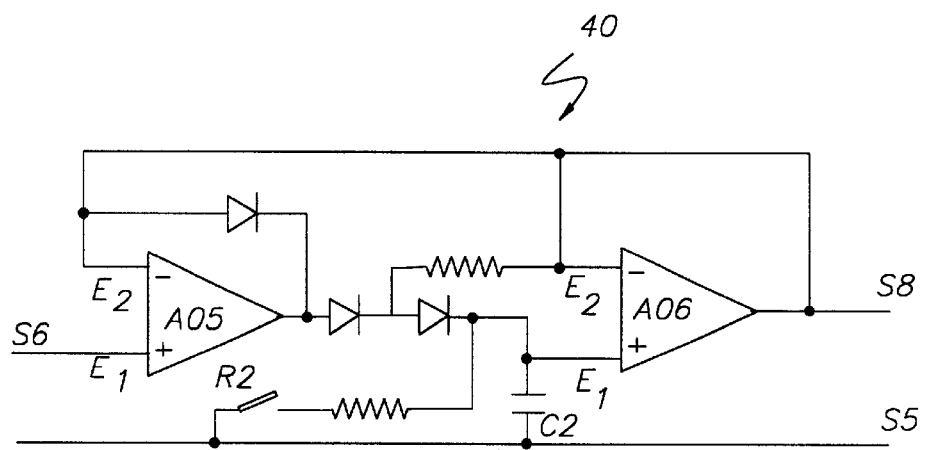
FIG. 5 shows a block diagram of the peak detector.

FIG. 5 shows a block diagram of the peak detector 40. The output s6 of the potentiostat 20 described above is linked to one input E1 of an operational amplifier AO5 so as to apply a voltage proportional to the current crossing the three-electrode cell 30. A second operational amplifier AO6 is used in the peak detector 40. One input E2 of AO6 is connected on the one hand to the AO5 output and on the other hand to the capacitor C2 described above. AO6 is mounted as a follow-up amplifier so as to reinject its output voltage to its second input E2 and to cancel its input voltage. The output voltage of AO6 is reinjected to the second input E2 of AO5. The capacitor C2 is charged until the output voltage of AO6 equals the potential of the input E1 of AO5. As the potential of the input E1 of AO5 increases, the capacitor C2 charges and the output voltage of AO6 equals that of the capacitor C2. When the potential of the input E1 of AO5 decreases, the capacitor C2 no longer charges and its potential stays constant. The output voltage of AO6 also stays constant. The output s8 of AO6 is linked to the display unit 50 that then shows a voltage value proportional to the current value corresponding to the height of the plateau of the current/voltage curve. A relay R2, controlled by the output s5 of the ramp generator 10, is provided to discharge C2 before carrying out a new measurement.

Figure 6:
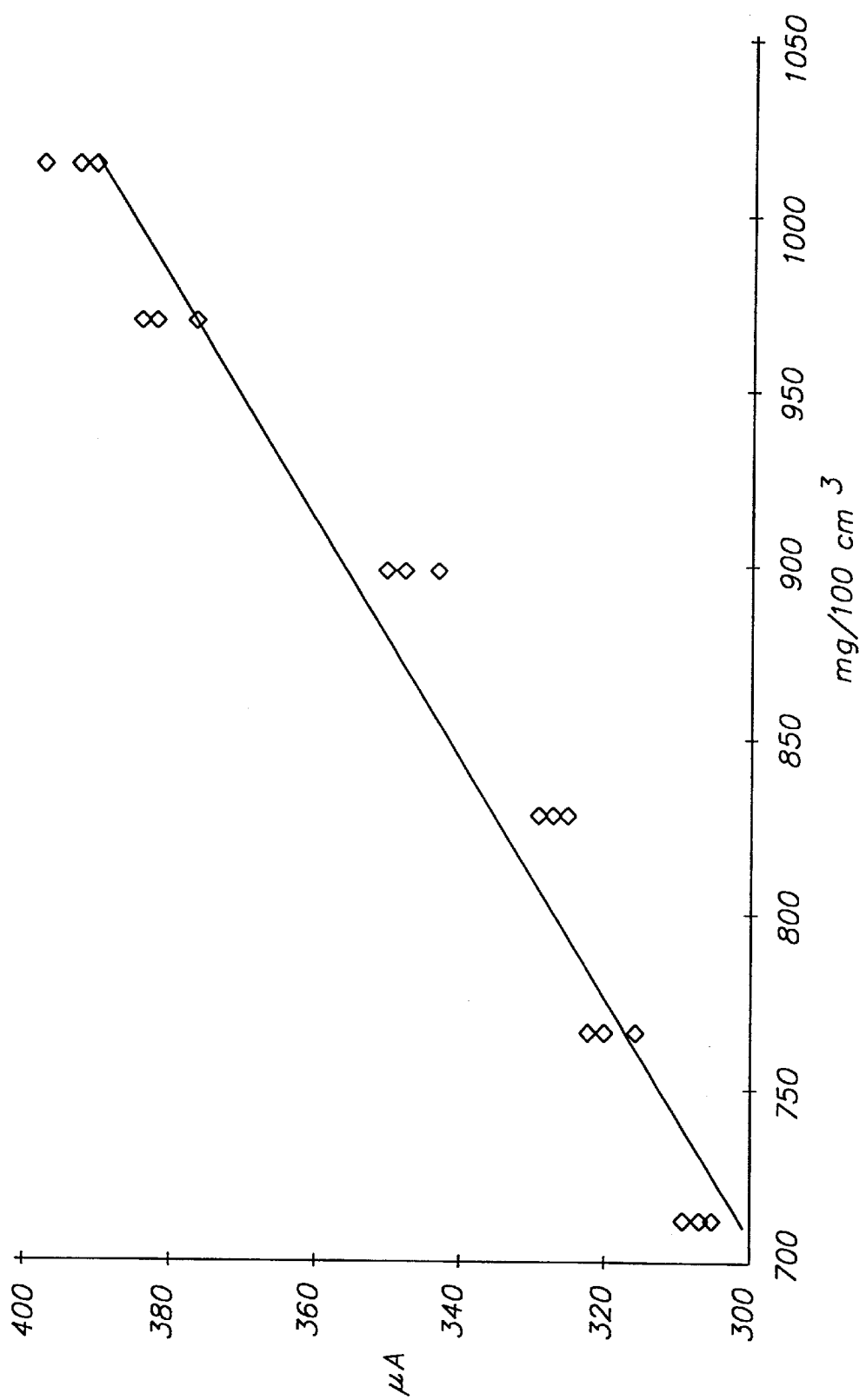
FIG. 6 shows a relationship between the maximum current measured by the device of the present invention and the ascobic acid concentration of the developing bath.

In one particular use of the invention, the device is used to measure the ascorbic acid concentration in developing baths. The measurement of ascorbic acid concentration allows bath replenishment to be controlled in order to obtain high quality products. The effluent volume is reduced. The linear relationship between the current measured by the device according to the invention and the concentration of ascorbic acid can be seen by referring to FIG. 6.

The device of the present invention is designed for carrying out measurements of the concentration of a defined developing agent, the voltage ramp being defined previously according to the developing agent. However, in one particular embodiment of the invention, a device can be provided to measure the concentration of various developing agents whether black and white developing agents of the family of aromatic polyhydroxyl compounds such as hydroquinone, hydroquinone monosulfonate, or color developing agents belonging to the paraphenylenediamines. Then various voltage ramps are used that allow the characteristic peak or plateau of the concentration of the developing agents to be seen. One potentiometer, not shown, is provided on the automatic measuring device for selecting the ramps according to the developing agent whose concentration is to be measured.

The operator who is to measure the concentration of a developing agent will only have to read the value shown by the display unit 50. A calculation chart is provided to convert the maximum current displayed by the invention device into concentration. The operator simply has to dip the electrode of the device in the solution, read the value displayed by the device and then convert the current value into concentration using the calculation chart.

It is obvious that a link can be provided with a computer to transfer the data, for example, to digitize the measured current value and to convert it using a conversion table before showing it on a display unit, or to make a statistical follow-up. It is also obvious that the compact three-electrode cell can be used together with a digital device for generating the voltage ramp and acquiring the maximum value.

The invention has been described in detail with particular reference to certain preferred embodiments thereof, but it will be understood that variations and modifications can be effected within the spirit and scope of the invention.

What is claimed is:

1. A device for automatically measuring a concentration of a developing agent in a solution, the device comprising:

a voltage generator capable of generating at least one voltage ramp provided to feed a three-electrode cell, the three-electrode cell comprising one reference electrode, one indicator electrode one auxiliary electrode, and a holder having three housing units, each housing unit being designed to accommodate one of said electrodes so as to hold the electrodes in fixed positions in relation to one another and to define an axis of orientation for said electrodes;

a potentiostat provided to maintain a constant potential difference between the indicator electrode and the reference electrode;

a peak detector provided to identify a maximum current flowing in said three electrode cell that corresponds to the developing agent concentration; and a display unit provided to show said maximum current;

wherein said auxiliary electrode has an angled end and a non-angled part with respect to said axis of orientation, said non-angled part of the auxiliary electrode being located outside the holder and being electrically insulated so as to create parallel and uniform current lines between said indicator electrode and said auxiliary electrode.

2. A device according to claim 1, wherein said holder is made of an electrically insulating material which is non-reactive to the contents of the developing agent.

3. A device according to claim 1, wherein an orifice is provided in the housing unit designed to accommodate the reference electrode, said orifice being provided to add a solution making up the reference electrode.

4. A device according to claim 1, wherein the voltage generator is capable of generating a plurality of ramps of different sweep rates.

5. A device according to claim 1, wherein the developing agent is ascorbic acid.

* * * * *